United States Patent [19]

Sturdivant

[11] 3,992,781
[45] Nov. 23, 1976

[54] ANTERIOR COTTON ROLL HOLDER

[76] Inventor: Jack E. Sturdivant, Oakwood Road, Rte. No. 4, Ames, Iowa 50010

[22] Filed: Dec. 15, 1975

[21] Appl. No.: 640,936

[52] U.S. Cl. .................................................. 32/35
[51] Int. Cl.² ......................................... A61C 5/12
[58] Field of Search .............................. 32/34–36

[56] References Cited
UNITED STATES PATENTS

| | | |
|---|---|---|
| 427,850 | 7/1909 | Gartrell ................................. 32/35 |
| 2,625,739 | 1/1953 | Garmers ............................... 32/35 |
| 2,897,597 | 8/1959 | Ivory ..................................... 32/35 |
| 3,739,477 | 6/1973 | Sturdivant ............................ 32/35 |

*Primary Examiner*—G.E. McNeill
*Attorney, Agent, or Firm*—Zarley, McKee, Thomte, Voorhees & Sease

[57] ABSTRACT

An anterior cotton roll holder comprised of an inverted L-shaped supporting post consisting of a vertical leg portion and a horizontal leg portion, a lower chin clamping portion slidably secured to the vertical leg portion, a first elongated arcuate cotton roll supporting member secured to an outer free end of said horizontal leg portion of said post, a second cotton roll supporting portion of arcuate shape concentrically positioned with respect to said first cotton roll supporting portion, and a vertically disposed inverted U-shaped connecting arm secured by ones of its ends to one of the ends of said first cotton roll supporting portion and secured by its other end to said second cotton roll supporting portion, and cotton rolls secured to the underneath surfaces of the first and second cotton roll supporting portions.

7 Claims, 5 Drawing Figures

ANTERIOR COTTON ROLL HOLDER

BACKGROUND OF THE INVENTION

Cotton roll holders have been previously provided for isolating the lower anterior teeth from the lips, cheeks and tongue so that the teeth may be maintained in a dry condition while dental work is being performed. The previous cotton roll holders were generally unsatisfactory due to the amount of space that they occupied in the patient's mouth which seriously hampered the performance of dental work. Applicant's cotton roll holders described in U.S. Pat. Nos. 3,805,389 and 3,739,477 represent a distinct improvement over the prior art devices and this invention represents an improvement over applicant's earlier devices. The instant invention is intended to be of the disposable type which eliminates the need for sterilization of the holders after use.

In addition, the anterior cotton roll holder of the present invention is an improvement over the devices of my prior patents in that it is less bulky and can therefore be used with less discomfort to the patient, can be molded easier than my prior devices and is therefore less expensive to manufacture, and generally represents an overall improvement in, in use performance characteristics as well as increased ease of handling, storage and manufacture.

Therefore, it is a principal object of the invention to provide an improved cotton roll holder.

A further object of the invention is to provide a lower anterior cotton roll holder.

A further object of the invention is to provide a disposable lower anterior cotton roll holder comprising a pair of concentrically positioned arcuate cotton roll supporting members, secured to one another by an inverted U-shaped connecting arm having cotton rolls secured to their underside by adhesive or the like.

A further object of the invention is to provide a lower anterior cotton roll holder which does not interfere with the performance of dental work and provides little patient discomfort.

A further object of the invention is to provide a lower anterior cotton roll holder which is comprised of a plastic material or the like, is easy to manufacture and of decreased size.

A still further object of the invention is to provide a cotton roll holder which is economical in manufacture, durable in use and refined in appearance.

These and other objects will be apparent to those skilled in the art.

BRIEF DESCRIPTION OF THE DRAWINGS

This invention consists in the construction, arrangements and combination of the various parts of the device, whereby the objects contemplated are attained as hereinafter more fully set forth, specifically pointed out in the claims, and illustrated in the accompanying drawings, in which:

DESCRIPTION OF THE PREFERRED EMBODIMENT

Figure 1:
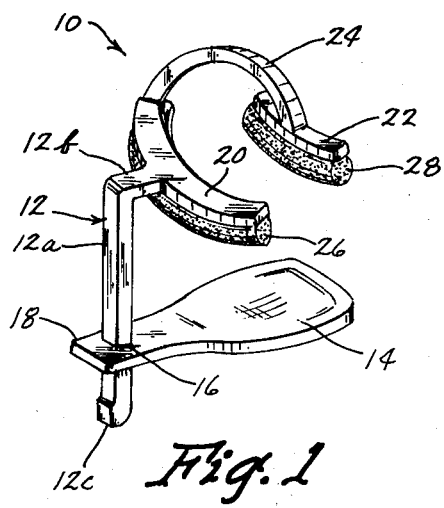
FIG. 1 is a perspective view of the anterior cotton roll holder of this invention.
Figure 2:
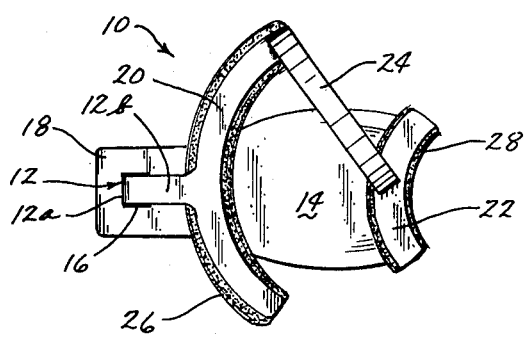
FIG. 2 is a top view of the cotton roll holder.
Figure 3:
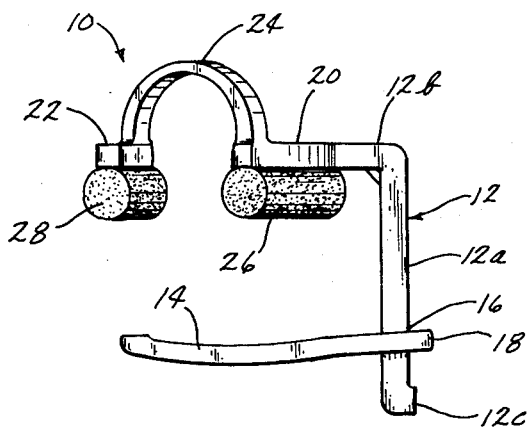
FIG. 3 is an elevated side view of the cotton roll holder of FIG. 1.
Figure 4:
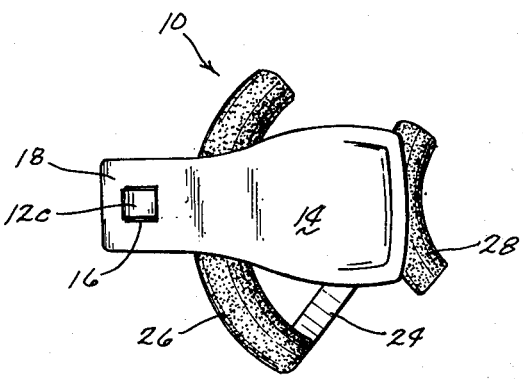
FIG. 4 is a bottom view of the cotton roll holder.

The cotton roll holder of FIG. 1 is referred to generally by reference numeral 10 and includes an inverted L-shaped supporting post 12 which itself is comprised of a vertical leg portion 12a which at its upper end joins a horizontal leg portion 12b and at its lower end terminates in a forwardly curved portion 12c. Positioned on inverted L-shaped support post 12 is a lower chin clamping spoon-shaped chin engaging plate 14. A slot 16 extends through handle portion 18 of chin plate 14 whereby the spoon-shaped chin plate 14 is selectively vertically adjustable along the length of vertical leg portion 12a of inverted L-shaped support post 12. Forwardly curved portion 12c prevents chin plate 14 from sliding off of vertical leg portion 12a.

Anterior cotton roll holder 10, as previously explained, includes a horizontally disposed and rearwardly extending leg portion 12b which joins the upper end of inverted L-shaped support post 12. The numeral 20 refers to a first elongated arcuate cotton roll supporting member which arcs rearwardly from horizontal leg portion 12b and which joins the end of horizontal leg portion 12b.

Figure 5:
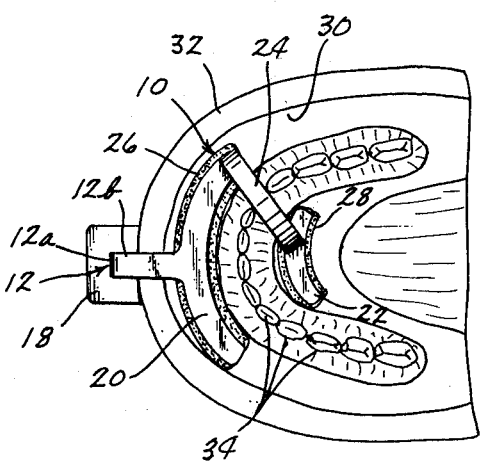
FIG. 5 is a top view of the holder in position in the mouth of the patient.

A second cotton roll supporting arcuate member 22 is concentrically positioned inwardly and rearwardly with respect to the first cotton roll supporting portion 20 and is held in position and joined to the first arcuate member 20 by a vertically disposed inverted U-shaped connecting arm 24. Connecting arm 24 is secured at one of its ends to one end of the first arcuate member 20 and secured by its other end to the second concentrically positioned cotton roll holder 22. Preferably connecting arm 24 is secured to one end of arcuate portion 20 and secured at its opposite end to the center of the second cotton roll supporting arcuate member 22. In this position, connecting arm 24, as seen in FIG. 5, is disposed away from the anterior teeth and does not interfere with dental work on those teeth. As can be seen from the drawings, and in particular FIG. 1 and FIG. 5, connecting arm 24 arcs over the teeth.

Cotton rolls 26 and 28 are secured by appropriate adhesive glue or the like to the undersides of arcuate members 20 and 22, respectively.

The anterior cotton roll holder 10 is positioned with respect to the patient's mouth as illustrated in FIG. 5, with spoon-shaped chin plate 14 adjusted to clamp under the patient's chin. The most forwardly positioned cotton roll 26 or labial cotton roll is attached to first arcuate member 20 and prevents the inside of the cheek 30 and the lips 32 from interfering with the anterior teeth 34. Correspondingly, the cotton roll 28 attached to the underside of the rearwardly positioned arcuate member 22 prevents the tongue from interfering with the working area for the anterior teeth 34 and is termed the lingual cotton roll.

Thus as can be seen the design of the cotton roll holder allows the dentist flexibility in isolating the lower anterior teeth for maximum dental work area while maintaining the teeth in a dry condition and provides a structure of limited bulkiness for ease of insertion in the mouth of the patient and for increased comfort of the patient during use of the device. The employment of the inverted U-shaped connecting arm 24 substantially eliminates the bulk of prior art anterior cotton roll holders making the device of the present invention more efficient, more economical for manufacture, more comfortable for the patient and more easy for use by the dentist.

Thus as can be seen, the invention accomplishes at least all of the stated objectives.

What is claimed is:

1. An anterior cotton roll holder comprising,
an inverted L-shaped supporting post consisting of a vertical leg portion and a horizontal leg portion having an outer free end,
a lower chin clamping portion slidably secured to said vertical leg portion,
a first elongated arcuate cotton roll supporting portion having first and second ends secured to the outer free end of the horizontal leg portion of said post,
a second cotton roll supporting portion of arcuate shape concentrically positioned with respect to said first cotton roll supporting portion,
a vertically disposed inverted U-shaped connecting arm secured by one of its ends to said first cotton roll supporting portion, and secured by its other end to said second cotton roll supporting portion, and
cotton rolls secured to the underneath surfaces of said first and second cotton roll supporting portions.

2. The anterior cotton roll holder of claim 1 wherein said connecting arm is secured by one of its ends to one of the ends of said first cotton roll supporting portion.

3. The anterior cotton roll holder of claim 2 wherein said connecting arm is secured by its other end to the center of said second cotton roll supporting portion.

4. The anterior cotton roll holder of claim 3 wherein said holder is comprised of low cost disposable material.

5. The anterior cotton roll holder of claim 4 wherein said holder is comprised of plastic material.

6. The device of claim 1 wherein said inverted L-shaped supporting post also includes at its bottom end a forwardly curved portion which restrains said chin clamp portion from sliding off of said inverted L-shaped supporting post.

7. The device of claim 6 wherein said chin clamping portion comprises a spoon-shaped member having a handle portion with said handle portion having a slot, said inverted L-shaped supporting post extending through said slot.

* * * * *